(12) United States Patent
Rakic et al.

(10) Patent No.: US 10,952,688 B2
(45) Date of Patent: Mar. 23, 2021

(54) MODULAR AND CONFIGURABLE COMPUTED TOMOGRAPHY SCANNING ASSEMBLY

(71) Applicant: XORAN TECHNOLOGIES, INC., Ann Arbor, MI (US)

(72) Inventors: Miodrag Rakic, Saline, MI (US); William C. Van Kampen, Saline, MI (US); Dejan Teofilovic, Ann Arbor, MI (US); Andrew J. Custer, Saline, MI (US)

(73) Assignee: XORAN TECHNOLOGIES, INC., Ann Arbor, MI (US)

( * ) Notice: Subject to any disclaimer, the term of this patent is extended or adjusted under 35 U.S.C. 154(b) by 32 days.

(21) Appl. No.: 16/364,058

(22) Filed: Mar. 25, 2019

(65) Prior Publication Data

US 2019/0298285 A1 Oct. 3, 2019

Related U.S. Application Data

(60) Provisional application No. 62/650,565, filed on Mar. 30, 2018.

(51) Int. Cl.
*A61B 6/00* (2006.01)
*A61B 6/04* (2006.01)
*A61B 6/03* (2006.01)

(52) U.S. Cl.
CPC ............ *A61B 6/4447* (2013.01); *A61B 6/035* (2013.01); *A61B 6/04* (2013.01); *A61B 6/4411* (2013.01)

(58) Field of Classification Search
CPC .... A61B 6/00; A61B 6/03; A61B 6/04; A61B 6/4447; A61B 6/035; A61B 6/4411; A61B 6/44; A61B 6/4429; A61B 6/4494; A61B 6/56; H05G 1/56
USPC ......... 378/4, 15, 17, 20, 101, 117, 193, 194, 378/195
See application file for complete search history.

(56) References Cited

U.S. PATENT DOCUMENTS

| 6,435,573 | B1 | 8/2002 | Szablewski |
| 6,609,826 | B1 | 8/2003 | Fujii et al. |
| 2004/0062357 | A1 | 4/2004 | Bair |
| 2005/0135560 | A1 | 6/2005 | Dafni et al. |
| 2008/0020332 | A1 | 1/2008 | Lavenda et al. |
| 2008/0063137 | A1 | 3/2008 | Hsieh et al. |
| 2008/0192885 | A1 | 8/2008 | Teofilovic et al. |
| 2012/0305723 | A1 | 12/2012 | Heath et al. |
| 2014/0043027 | A1 | 2/2014 | Overweg |
| 2014/0205060 | A1 | 7/2014 | Kim et al. |

OTHER PUBLICATIONS

International Search Report for International Application No. PCT/US2019/023939, dated Jun. 11, 2019, 4 pgs.

*Primary Examiner* — Jurie Yun
(74) *Attorney, Agent, or Firm* — Dickinson Wright PLLC

(57) ABSTRACT

A computed tomography system is disclosed with a gantry assembly and a base assembly. The gantry assembly having a x-ray source, and a x-ray imager. The base assembly is configured to receive power and provide mechanical stability. A connection interface is located between the gantry assembly and the base assembly. The connection interface is configured to mechanically lock the gantry assembly to the base assembly and provide power to the gantry assembly through the base assembly.

24 Claims, 12 Drawing Sheets

MODULAR AND CONFIGURABLE COMPUTED TOMOGRAPHY SCANNING ASSEMBLY

CROSS REFERENCE TO RELATED APPLICATIONS

This application claims the benefit of U.S. Provisional Patent Application No. 62/650,565 filed Mar. 30, 2018, the content of which is hereby incorporated by reference in its entirety.

BACKGROUND

1. Field of the Invention

The present disclosure generally relates to a computed tomography system.

2. Description of Related Art

Computed tomography systems are great diagnostic tools. However, the cost of the technological components limit the number of systems that are available to a facility. Further, repair and diagnostics of these systems becomes very time critical when they are down due to their usefulness and low supply. Further for a stationary system, onsite updates, maintenance, and quality control procedures may require a medical physicist on site, which can be complicated and expensive.

In view of the above, it is apparent that there exists a need for a system for an improved computed tomography system.

SUMMARY

In satisfying the above need, as well as overcoming the enumerated drawbacks and other limitations of the related art, the present disclosure provides an improved computed tomography system.

Specialized, point of care medical imaging devices are becoming more mainstream and more capable, for example cone-beam computed tomography systems can now be found in doctor's offices and even the operating room. As competing scanners enter the market, capital equipment prices have eroded, and the service has become an increasing share of the business model. Here also competition is creating downward price pressure, and the existing methods of sending technicians on-site to install and service devices is becoming cost-prohibitive. Furthermore, most currently available systems are largely limited to installation in fixed locations, and not well-suited for more challenging applications such as vehicle-based platforms.

The concept presented here is a modular medical imaging system platform that would be easier to install and service and would have the flexibility to evolve as the end user's needs change and the technology evolves to support more challenging applications. The detachable imaging module would economize installation, maintenance, upgrades, and even allow one device to be used in multiple locations. The generalized imager attachment point serves to mount any one of several imaging module variations, depending on the application. Modular control electronics enable a suite of compatible components (imaging arm, wall mount, cart, upright, chair, shielding, vehicle mount point, robotic arm) to be developed for each application, and communicate with each other and the parent system within a common framework.

DETAILED DESCRIPTION

Figure 1:
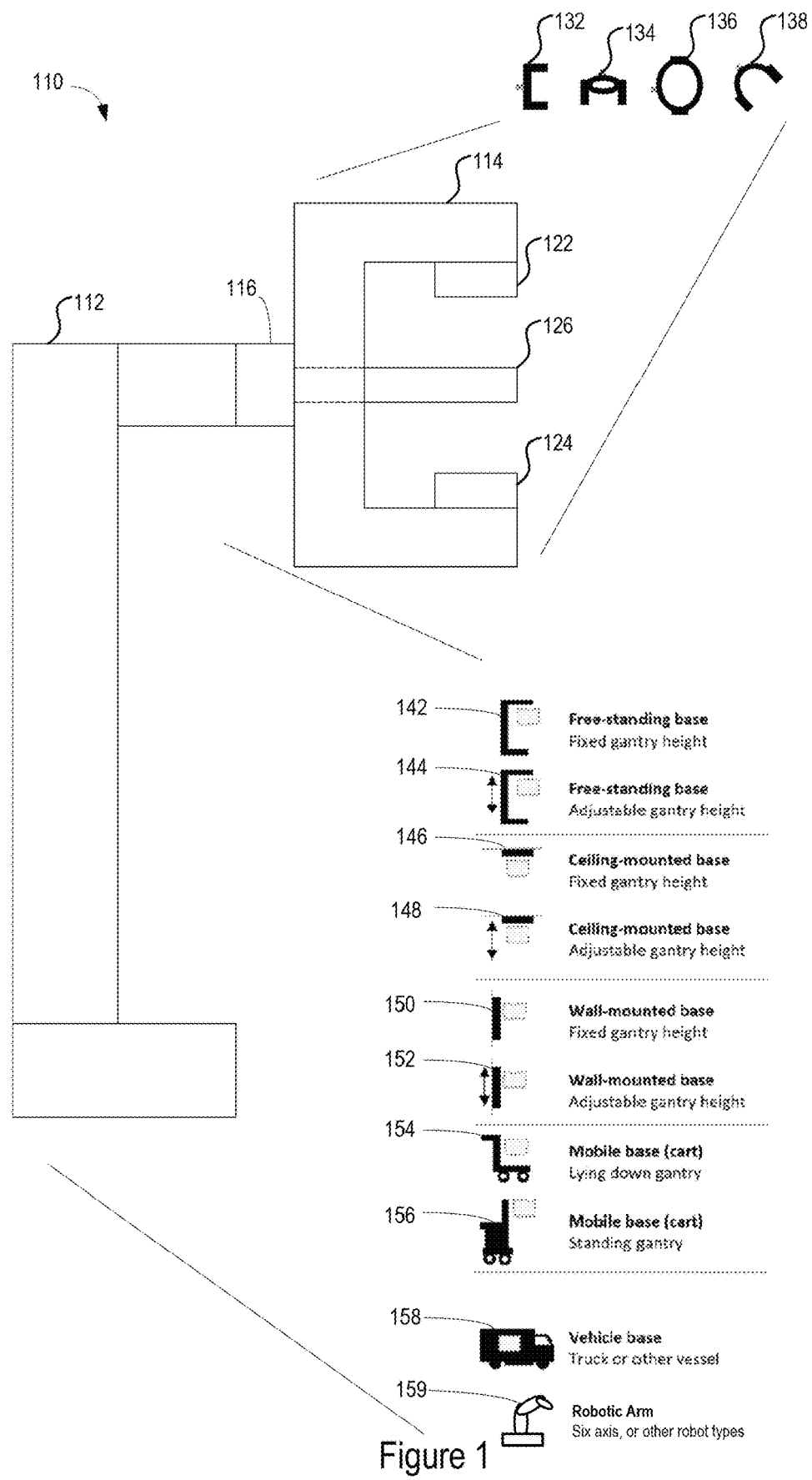
FIG. 1 is a schematic view of a computed tomography system.

The improved computed tomography system may have a detachable imaging module. The detachable imaging module may be a gantry assembly with an x-ray source and an x-ray imager. The detachable imaging module may be user installable and replaceable. The detachable imaging module can fit into FedEx shipping crate to send back for centralized service, or rapid replacement. The detachable imaging module can take different forms: U, C, O, and different sizes for targeted applications as discussed in more detail later with regard to FIG. 1. The detachable imaging module may be self-contained, with all elements that would need maintenance or updates. The various forms of imaging modules may have a common interface attachment point. The common interface may be a socket assembly. The common interface attachment may include safety features to enable user-replacement. The safety features may include a locking mechanism and connector that support two person lift and connect with a two-point safety disconnect.

The detachable imaging module may include an integrated patient positioning device mounted to non-rotating interior portion of the imaging arm. The integrated patient positioning device prevents need for separate chair or table and reduces the need to identify the location of the chair or table relative to the detachable imaging module. The common attachment point provides a mechanical support, power, high speed data connection, and locking mechanism. The common attachment point may not require specialized service, calibration or adjustment (or very infrequent). Further, the common attachment point may be configured to not rotate with the gantry (e.g. remain stationary with respect to the base assembly). The common attachment interface may be fixed point or mobile (e.g. may go up or down) or may mount on a ceiling, wall, moveable cart or arm, vehicle, ambulance (inside or outside), truck or ship. The common attachment interface may be connected to the end of a robotic arm (e.g. a six axis industrial robot). The sensed information or data coming from the base assembly (e.g. including the robot arm) could be the robots pose information (e.g. joint angles, link lengths, etc.), position in space of the common attachment interface, or its acceleration or velocity. This could feed information to the reconstruction engine for example about how to reconstruct the dataset. (e.g. circular orbit, vs helical, vs complex). This position or movement information could also inform the user interface as discussed throughout this document, what scanning protocols are enabled, etc.

The detachable imaging module may contain modular control electronics. The modular control electronics may include a standard interface protocol (e.g. CAN bus) enabling all internal elements to be controlled and configured remotely such as shutter, sensors, motor controller, x-ray source, etc. for troubleshooting, upgrading firmware, or diagnostic tests. The modular control electronics may have the same communication framework enabling communication between the parent imaging module and to accessory items. For example, detection of the patient positioning device, presence or absence of patient, patient weight or position, temperature of room, temperature of x-ray source, vehicle movement, etc.

The modular control electronics may include enabling future "plug and play" interchangeability of components for further modularity, upgrades and ease of service, (e.g. new detector panel model, or upgraded collimators, etc.). The modular control electronics may facilitate calibrations, adjustments, safety tests and updates that can be performed remotely, or automated. One implementation of a gantry assembly is provided in U.S. Pat. No. 7,379,524, issued May 27, 2008.

FIG. 1 is a schematic view of one possible implementation of a computed tomography system including a base assembly such as base assembly 112, a gantry assembly 114, and connection interface 116 (such as a socket assembly). The gantry assembly 114 may include an x-ray generator 122 and a x-ray detector 124. The x-ray generator 122 may project an x-ray beam at a target (e.g. a patient) that may be located on an integrated patient positioning accessory or test object 126. The x-ray beam may project through the target and be imaged by the x-ray detector 124. The gantry assembly 114 may take many forms and multiple different gantry assemblies 114 may interface interchangeably with multiple different base assemblies through a connection interface 116 (e.g. that provides mechanical locking and support, as well as, electrical connectivity) such as a universal socket assembly. The gantry assembly 114 may be a simple block shaped assembly 132 with a straight base section and two arms sections extending from the base section, for example in a substantially parallel arrangement. The gantry assembly 114 may be an oval base assembly 134 with an oval base section and two arms sections or just the x-ray generator and x-ray detector extending from the base section, for example in a substantially parallel arrangement. The gantry assembly 114 may be an oval assembly 136 with an oval section where the x-ray generator and the x-ray detector are attached to opposite sides base section such that the x-ray beam is directed through the oval. The gantry assembly 114 may be a simple "C" shaped assembly 138 with a curved base section extending into two arm sections, for example extending in a substantially parallel arrangement.

The base assembly 112 may take one of many forms all of which may include the universal connection interface 116 to connect with any of the gantry assemblies 114 described herein. The base assembly 112 may be a free-standing base 142 with a fixed gantry height. The base assembly 112 may be a free-standing base 144 with an adjustable gantry height. The gantry height may be adjustable via a motor assembly or a manual adjustment. Sensors may determine the gantry height and provide the information to the local processing unit connected to the base assembly 112 as well as to the processor located on the gantry through the universal connection interface 116.

The base assembly 112 may be a ceiling mounted base 146 with a fixed gantry height. The base assembly 112 may be a ceiling mounted base 148 with an adjustable gantry height. The gantry height may be adjustable via a motor assembly or a manual adjustment. Sensors may determine the gantry height and provide the information to the local processing unit connected to the base assembly 112 as well as to the processor located on the gantry through the universal connection interface 116.

The base assembly 112 may be a wall mounted base 150 with a fixed gantry height. The base assembly 112 may be a wall mounted base 152 with an adjustable gantry height. The gantry height may be adjustable via a motor assembly or a manual adjustment. Sensors may determine the gantry height and provide the information to the local processing unit connected to the base assembly 112 as well as to the processor located on the gantry through the universal connection interface 116.

The base assembly 112 may be a mobile base 154 (e.g. a cart) with the gantry lying down. The base assembly 112 may be a mobile base 156 (e.g. a cart) with an adjustable gantry height. The mobile base 154 and the mobile base 156 may have a fixed gantry height or an adjustable gantry height. The gantry height may be adjustable via a motor assembly or a manual adjustment. Sensors may determine the gantry height and provide the information to the local processing unit connected to the base assembly 112 as well as to the processor located on the gantry through the universal connection interface 116.

The base assembly 112 may be a vehicle base 158, for example, a truck, car, or other vessel. Vehicle base 158 may have a fixed gantry height or an adjustable gantry height. The gantry height may be adjustable via a motor assembly or a manual adjustment. Sensors may determine the gantry height and provide the information to the local processing unit connected to the base assembly 112 as well as to the processor located on the gantry through the universal connection interface 116.

The base assembly 112 may be a robotic arm base 159, for example, six axis industrial or other robot type. Robotic arm base 159 may have adjustable position and orientation of the universal connection interface 116. Sensors may determine the position and orientation of the robot (e.g. through robot pose or other sensors) or the universal connection interface 116 and provide the information to the local processing unit connected to the base assembly 112 as well as to the processor located on the gantry through the universal connection interface 116.

The base assembly 112 and gantry assembly 114 may communicate various signals through the connection interface. The signals communicated may include balance and/or wobble of the base assembly and/or gantry assembly, acceleration of the base assembly or gantry assembly, robot position or pose information of any robotic assembly included in the base assembly, temperature of the room, temperature of the detector, temperature of the source, rotation effort (e.g. current provided to the motor or torque), presence of the patient or object, the type of patient positioning surface attached (e.g. the patient positioner may have an ID that can be transmitted via wired or wireless connection, such as RFID, WiFi, bluetooth, etc.) to identify the type of positioner such as head holder, arm rest, leg rest etc., presence of a cart or transport, power condition, battery condition, WiFi environment (e.g. Wifi sources available, noise, traffic), handle sensors, vehicle status (e.g. vehicle running, vehicle parked, vehicle moving, vehicle level, vehicle acceleration in each direction, temperature, vehicle power status, mounting inside or outside the vehicle, etc.). The patient positioner may also include one or more sensors to determine if the patient is present, absent, moving, or stationary, as well as, the weight and size of the patient.

In addition, the system may include an emergency stop control. The wiring and control electronics for emergency stop ("E-Stop") may go through the base unit. (cart, arm, wall mount, etc). The emergency stop may be a button that is pressed to halt the x-ray and gantry motion. The emergency stop may send a signal to the gantry motor and x-ray control electronics through the connection interface. The emergency stop may have a dedicated connection for just the emergency stop signal for example one of the contacts described below and/or shown with regard to FIG. 12.

Contacts on the gantry assembly may make electrical connection with contacts in the connection interface (e.g. socket assembly). For example, contacts on the spindle may make an electrical connection (e.g. physical contact) with the contacts in the socket. The contacts on the spindle may forced into contact with the contacts in the socket by one or both of the locking mechanism that mechanically lock the spindle into the socket.

Each gantry assembly may include the features described with respect to every other gantry assembly described elsewhere in this document. Further, any of the gantry assemblies may interface with any of the other base stands described throughout this disclosure.

Figure 2:
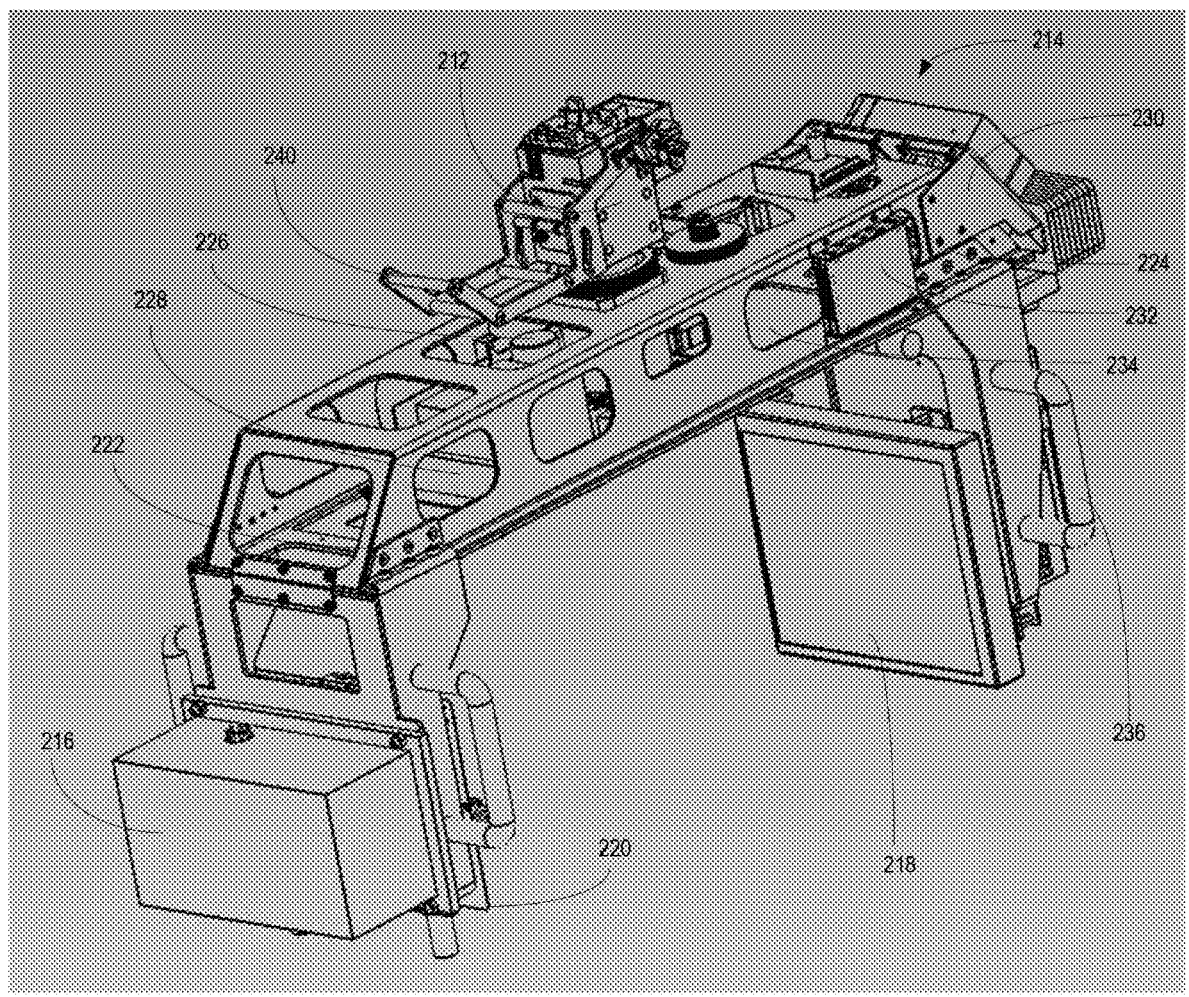
FIG. 2 is a perspective view of a gantry assembly and socket assembly.

FIG. 2 is a perspective view of a gantry assembly 214 and socket assembly 212. The socket assembly 212 may be integrated into one of many different stands located throughout a facility. Each stand may have an identical socket assembly 212 allowing one or more gantry assemblies 214 to be moved between stands and shared when necessary. The gantry 214 includes an x-ray detector panel 218 and x-ray generator 216. The x-ray generator 216 generates an x-ray beam that is directed a portion of the patient located between the x-ray generator 216 and the x-ray detector panel 218. The x-ray beam interacts with the portion of the patient and is imaged by the x-ray detector panel 218. The position of the x-ray generator 216 and x-ray detector panel 218 may be moved around a portion of the patient to be inspected such that x-ray images may be collected at multiple orientations to generate a computer tomography (CT) model that may be used to diagnose the patient. A beam limiter board 220 may be positioned between the x-ray generator 216 and the x-ray detector board 218 to condition the x-ray beam appropriately. The x-ray generator 216 may be attached to a gantry frame through a joint 222. Using the joint allows a modular design that facilitates removal and replacement of the x-ray generator 216. Similarly, the x-ray detector panel 218 may be attached to the gantry frame through joint 224 providing a modular design that facilitates removal and replacement of the x-ray detector panel 218 when necessary. An encoder 226 monitors the gantry's radial position as the gantry assembly 214 is rotated about a spindle attaching the gantry assembly 214 to the socket assembly 212. The gantry assembly 214 may include an onboard computer 228. In addition, the gantry assembly 214 may include a counterweight and power supply assembly 230. Further, the gantry assembly may include controlling electronics, for example solid state drives 232 and a distribution board 234. The gantry assembly 214 may also include at least one carrying handle 236 for moving the gantry assembly 214 from stand to stand. The on-board circuitry may require that two operators must simultaneously touch all four carrying handles with a lock handle 240 being raised to release the safety interlock. Such a safety release mechanism may provide protection for both the gantry assembly 214 but also the operators that move the gantry assembly 214.

Figure 3:
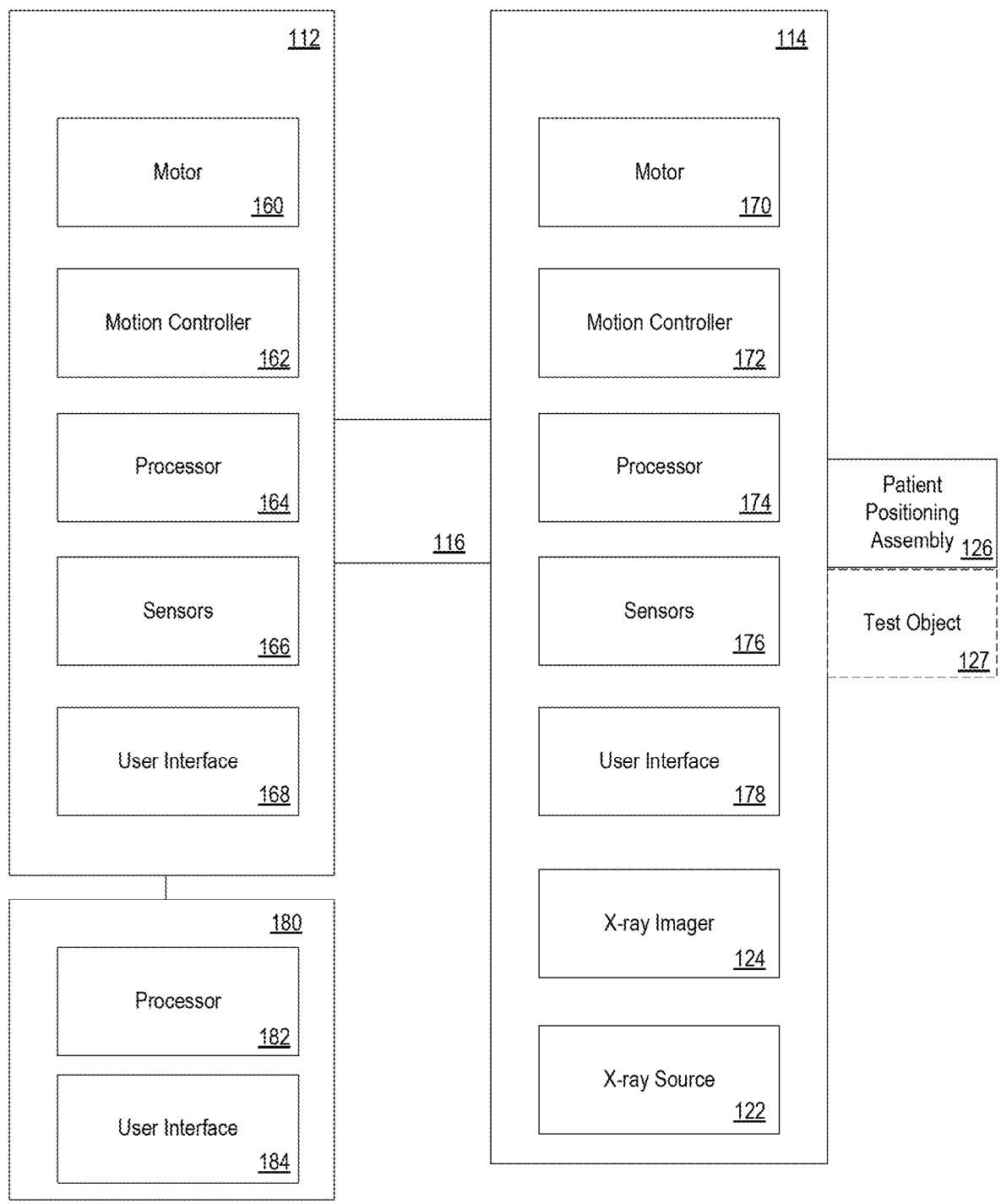
FIG. 3 is a block diagram of the computed tomography system

FIG. 3 is a block diagram of a computed tomography system. The system includes a base assembly 112, a gantry assembly 114, and connection interface such as a connection interface 116 (such as a socket assembly). As described elsewhere, the connection interface 116 connects the gantry assembly 114 to the base assembly 112. The base assembly 112 may include one or more motors 160 to manipulate the position and orientation of the connection interface 116. The one or more motors 160 may be controlled by a motion controller 162. The base assembly 112 may include sensors 166 for monitoring the location and orientation of the connection interface 116 or conditions relevant to the base assembly 112 or connection interface 116, for example if the lock lever is in the locked or unlocked position or whether the spindle of the gantry assembly 114 is fully inserted into the connection interface 116, or other attributes as discussed elsewhere. The base assembly 112 may include a processor 164 for processing, storing, and analyzing data from the other components in the computed tomography system. The processor 164 may be in communication with the processor in the gantry assembly 114 or a processor 182 in a remote station 180. The processor 164 may share information with the other processors regarding the status of any of the mentioned components, image data, or position and orientation information about the connection interface. Further, a user interface 168 may allow a user access to any of the functionality in any of the components including the base assembly, connection interface, or gantry assembly.

The gantry assembly 114 may include an x-ray generator 122 and a x-ray detector 124. The x-ray generator 122 and x-ray detector 124 may be controlled by one or more processors 174. The gantry assembly 114 may include one or more motors 170 to manipulate the position and orientation of the gantry assembly 114. The one or more motors 170 may be controlled by a motion controller 172. The gantry assembly 114 may include sensors 176 for monitoring the location and orientation of the gantry assembly 114, location and orientation of the patient positioning surface, or conditions relevant to the gantry assembly 114, for example if the handles for carrying the gantry assembly 114 are being grasped or other attributes discussed elsewhere in the application. The gantry assembly may include a processor 174 for processing, storing, and analyzing data from the other components of the gantry assembly 114. The processor 174 may be in communication with the processor in the base assembly 112 or a processor 182 in a remote station 180. The processor 174 may share information with the other processors regarding the status of any of the mentioned components, image data, or position and orientation information about the gantry assembly. Further, a user interface 178 may allow a user access to any of the functionality in any of the components including the base assembly, connection interface, or gantry assembly.

A remote station 180 may also be connected to the gantry assembly 114 through the base assembly 112 and connection interface 116. The remote station 180 may be located in the same room as the base station 112 or at a different premises. The processor 182 may be in communication with the processor in the base assembly 112 or the gantry assembly 114. The processor 182 may share information with the other processors regarding the status of any of the mentioned components, image data, or position and orientation information about the gantry assembly. Further, a user interface 184 may allow a user access to any of the functionality in any of the components including the base assembly, connection interface, or gantry assembly.

In some implementations, the base assembly 112 may have a variety of sensors that may be used to measure various attributes of the base assembly. The base assembly 112 may then communicate the measured attribute to another component of the system, for example the gantry assembly 114 through the connection interface 116 and/or a user interface (e.g. in the remote station 180, the base assembly 114 and/or the gantry assembly 112), which may be used for controlling one or more parameters of the other component. The base assembly 112 may also evaluate the attribute, for example by applying a threshold or other analysis, to generate a command to control the other component (e.g. the gantry assembly 114 through the connection interface 116 and/or the user interface).

In some implementations, the gantry assembly 114 and/or the patient positioning accessory may have a variety of sensors that may be used to measure various attributes of the gantry assembly 114 and/or patient positioning accessory. The gantry assembly 114 and/or the patient positioning accessory may then communicate the measured attribute to another component of the system, for example the base assembly 112 through the connection interface 116 and/or a user interface (e.g. in the remote station 180, the base assembly 114 and/or the gantry assembly 112), which may be used for controlling one or more parameters of the other component. The gantry assembly 114 and/or the patient positioning accessory may also evaluate the attribute, for example by applying a threshold or other analysis, to generate a command to control the other component (e.g. the base assembly 112 or the user interface through the connection interface 116).

More specifically, the base assembly 112 may include a motion sensor, acceleration sensor, vibration sensor, tilt sensor, or otherwise sense non-level conditions. The base assembly 112 may communicate the measured data from one or more of the sensors or a command in response to analysis of the data to the user interface, the gantry controller, or the x-ray source. The user interface may issue a warning to the user in response to the data or command (e.g. if the data is above a given threshold, such as a movement threshold or acceleration threshold). The gantry controller may prevent motion of the gantry assembly 114 and/or lock the position of the gantry in response to the data or command. The x-ray source may stop operation or shut down in response to the data or command.

The base assembly 112 may include environmental temperature sensor, such as an ambient temperature sensor or a base temperature sensor. The base assembly 112 may communicate the measured data from one or more of the temperature sensors or a command in response to analysis of the data to the user interface, the gantry controller, or the x-ray source. The user interface may issue a warning to the user in response to the data or command (e.g. if the data is above or below a given threshold, such as a temperature threshold). The gantry controller may prevent motion of the gantry assembly 114 and/or lock the position of the gantry in response to the data or command. The x-ray source may stop operation or shut down in response to the data or command.

The base assembly 112 may include power supply status sensors, such as a voltage sensor or a current sensor. The base assembly 112 may communicate the measured data from one or more of the power supply status sensors or a command in response to analysis of the data to the user interface, the gantry controller, or the x-ray source. The user interface may issue a warning to the user in response to the data or command (e.g. if the data is above or below a given threshold, such as a voltage or current threshold). The gantry controller may prevent motion of the gantry assembly 114 and/or lock the position of the gantry in response to the data or command. The x-ray source may be limited in operation, prevented from firing or shut down in response to the data or command (e.g. if power is not sufficient).

The base assembly 112 may include backup power status sensors, such as position voltage or current sensors to monitor presence and condition of battery backup (e.g. uninterruptible power supply (UPS) status sensors). The sensors may operate to determine presence, absence, or status (e.g. by physical position, voltage, or current). The base assembly 112 may communicate the measured data from one or more of the backup power status sensors or a command in response to analysis of the data to the user interface, the gantry controller, or the x-ray source. The user interface may issue a warning to the user in response to the data or command (e.g. if the data is above or below a given threshold, such as a position, voltage or current threshold). The warning may indicate the need for a replacement back up power, such as a battery. The system may also notify a customer service agent at the supplier through for example email, text, or phone communication. The notification may include the type of base, a serial number, the measured data from the sensors, an error code, as well as, other identifying and/or diagnostic information. The gantry controller may prevent motion of the gantry assembly 114 and/or lock the position of the gantry in response to the data or command. The x-ray source may be limited in operation, prevented from firing or shut down in response to the data or command (e.g. if power is not sufficient).

The base assembly 112 may include accessory sensors, for example configured to determine presence of an accessory (e.g. USB, disk drive, data storage, input devices keyboard, monitor). The base assembly 112 may communicate the measured data from one or more of the accessory sensors or a command in response to analysis of the data to the user interface, the gantry controller, or the x-ray source. The user interface may issue a warning to the user in response to the data or command (e.g. if storage device is full or otherwise unable to store the scan). The gantry controller may prevent motion of the gantry assembly 114 and/or lock the position of the gantry in response to the data or command. The x-ray source may be limited in operation, prevented from firing or shut down in response to the data or command (e.g. the storage device is unable to store the scan) The system may also enable or disable input controls, overriding alternative input devices (e.g. controls on the gantry). The system may also automatically select a default data storage device to replace a specified storage device when the specified storage device is full or unavailable.

The base assembly 112 may include network diagnostic electronics, for example configured to determine presence, speed, and/or quality of an internet connection. The base assembly 112 may communicate the measured data from the network diagnostic electronics or a command in response to analysis of the data to the user interface or other components. The user interface may issue a warning to the user in response to the data or command (e.g. if there is no internet connection or the connection is degraded). The control electronic of the system may adjust settings for automatically pushing image data over the network, data size, compression factors, image quality etc. in response to the determined network quality, speed, or other network attributes.

The base assembly 112 and/or the gantry assembly 114 may include interface lock sensors, for example determining the position of locking pins, actuation or deactivation of the solenoid, position of the locking handle, or other attributes of the locking mechanisms. The base assembly 112 and or gantry assembly 114 may communicate the measured data from one or more of the interface lock sensors or a command in response to analysis of the data to the user interface, base assembly control circuitry, the gantry controller, or the x-ray source. The user interface may issue a warning to the user in response to the data or command (e.g. if the data is above a given threshold, such as a position threshold). The gantry controller may prevent motion of the gantry assembly 114 and/or lock the position of the gantry in response to the data or command. The x-ray source may be limited in operation, prevented from firing or shut down in response to the data or command. The control electronics may also kill power, or initiate a "graceful" shut down sequence for the onboard computers.

The gantry assembly 114 and/or the patient positioning accessory may have target sensors to determine presence or absence of patient or object in the field of view of the x-ray imager 124. These sensors may include proximity sensors, imaging sensors, physical position sensors, or other sensing devices. The gantry assembly 114 and/or the patient positioning accessory may communicate the measured data from one or more of the target sensors or a command in response to analysis of the data to the user interface, base assembly control circuitry, the gantry controller, or the x-ray source (e.g. the user interface and base assembly 112 through the connection interface 116). The user interface may issue a warning to the user in response to the data or command (e.g. if the data is above a given threshold, such as a position threshold). The gantry controller may prevent motion of the gantry assembly 114 and/or lock the position of the gantry in response to the data or command. The x-ray source may be limited in operation, prevented from firing or shut down in response to the data or command. The system may further enable or disable appropriate scanning protocols or calibration methods (e.g. Air calibration requires no patient) in response to the data or command. For example, if no patient is present an air calibration option may be presented to the user on the user interface or automatically initiated. Other examples are provided in more detail below.

The gantry assembly 114 and/or the patient positioning accessory may have patient sensors to detection of patient body part (e.g. head, hand, face, foot). The detection of the body part can be identified, for example through a unique plug in of a body part holder, such as patient position accessory 126 or test object 127 (e.g. phantom). The patient position accessory 126 or test object may communicate a unique identification or accessory type identification when plugged into the system. As such, the patient body type may be used to determine the body part that will be inspected. The sensors may include proximity sensors, imaging sensors, physical position sensors, or other sensing devices. The gantry assembly 114 and/or the patient positioning accessory may communicate the measured data from one or more of the target sensors or a command in response to analysis of the data to the user interface, base assembly control circuitry, the gantry controller, or the x-ray source (e.g. the user interface and base assembly 112 through the connection interface 116). The user interface may provide particular configuration options based on the type of body part detected. The gantry controller may adjust the speed or motion of the gantry in response to the data or command based on the determined body part. The x-ray source may adjust x-ray parameters for example intensity or beam shape in response to the data or command. As such the control circuitry of the system may determine and enable appropriate available scanning protocols and reconstruction settings for the body part.

The gantry assembly 114 and/or the patient positioning accessory may have calibration sensors to determine of which specific test object is in the field of view of the x-ray imager 124. The test object may be identified through unique plug in of the object holder, such as discussed with regard to patient position accessory 126. The test object holder may communicate a unique identification or accessory type identification when plugged into the system. As such, the test object holder may be used to determine the test object type that will be inspected. The sensors may include proximity sensors, imaging sensors, physical position sensors, or other sensing devices. The gantry assembly 114 and/or the patient positioning accessory may communicate the measured data from one or more of the target sensors or a command in response to analysis of the data to the user interface, base assembly control circuitry, the gantry controller, or the x-ray source (e.g. the user interface and base assembly 112 through the connection interface 116). The user interface may provide particular configuration options based on the particular test object detected. The gantry controller may adjust the speed or motion of the gantry in response to the data or command based on the determined test object. The x-ray source may adjust x-ray parameters for example intensity or beam shape in response to the data or command. The system control circuit may put the system in the appropriate testing mode which can affect scan acquisition parameters, as well as reconstruction techniques and post imaging analysis tools to be initiated. The system may issue the appropriate messages to the user and send reports to a customer service agent for monitoring and oversight.

The gantry assembly 114 and/or the patient positioning accessory may have patient sensors to determine the size and weight of the patient. These sensors may include weight sensors, proximity sensors, imaging sensors, physical position sensors, or other sensing devices. The gantry assembly 114 and/or the patient positioning accessory may communicate the measured data from one or more of the target sensors or a command in response to analysis of the data to the user interface, base assembly control circuitry, the gantry controller, or the x-ray source (e.g. the user interface and base assembly 112 through the connection interface 116). The user interface may provide particular configuration options based on the weight or size of the patient detected. The gantry controller may adjust the speed or motion of the gantry in response to the data or command based on the size or weight of the patient. The x-ray source may adjust x-ray parameters for example intensity or beam shape (e.g. x-ray beam collimation (a.k.a. "shutterboard") in response to the data or command. The system control circuit may determine and enable appropriate available scanning protocols or default settings (e.g. pediatric protocols are lower radiation for smaller or lighter patients, require lower kVp and mA scan parameters as such these parameters may be changed based on the sensor data). The system may affect the control of x-ray beam shape via collimators to expose the appropriate patient anatomy and limit unnecessary exposure.

The gantry assembly 114 may have gantry sensors to determine rotational balance, tip, tilt, or motor power consumption during rotation of the gantry. These sensors may include accelerometers, gyroscopes, or other sensing devices. The gantry may communicate the measured data from one or more of the gantry sensors or a command in response to analysis of the data to the user interface, base assembly control circuitry, the gantry controller, or the x-ray source (e.g. the user interface and base assembly 112 through the connection interface 116). The user interface may issue a warning to the user in response to the data or command (e.g. if the data is above a given threshold, such as an acceleration, tip, tilt or power threshold). The system may also send an alert to a customer service agent (e.g. including the data measured by the gantry sensor). The gantry controller may prevent motion of the gantry assembly 114 and/or lock the position of the gantry in response to the data or command. The system control circuitry may detection an out of balance conditions and may be configured automatically rebalance itself in some implementations. The x-ray source may be limited in operation, prevented from firing or shut down in response to the data or command.

Different specific scan techniques may be utilized for different objects during system calibration, characterization, performance monitoring and quality control. A scan technique (sometimes also called a scan "protocol") can include a large number of specific settings for example as discussed in the paragraph below.

X-ray settings may include: peak tube voltage (kVp), tube current (mA), number of projection frames/x-ray pulses, and pulse rate. Detector settings may include: effective pixel size, pixel binning, frame rate, readout gain and type, subframe readout (portion of detector that is exposed). Gantry settings may include: orbit type (e.g. circular vs spiral vs multi-circular), orbit length (e.g. 360 degrees, or 240 or 720, etc), rotation rate (speedup, slowdown, rewind settings). Reconstruction settings may include: reconstruction mode (traditional "FDK" filtered back projection versus "iterative reconstruction", or other more advanced techniques e.g. machine learning deep convolutional networks, reconstruction filter type (e.g. Ramp or Hamming) and cutoff frequency settings, computer mode (e.g. GPU or CPU processing), memory handling (e.g. flash memory, or use of data subset), image slice thickness (Voxel size), and corrections for bony skull or metal artifact or patient movement. Viewing or export settings may include Display contrast "window/level", multiplanar view or 3D view or MIP (maximum intensity projection), and export type (e.g. DICOM push to PACS).

Each of the above settings (parameters) may be adjusted in response to the sensed measurements discussed throughout this application. For example, each of the settings above may be adjusted in response the sensed conditions described above including for example, type of gantry, type of calibration objects, type of patient positioning surface, type of body part being measured, motion, acceleration, vibration, tilt, ambient temperature, base temperature, power supply status, voltage, current, power, position, lock status, image data, and patient size or weight.

Some examples of adjusting system settings in response to the measured attributes may include patient scanning, as well as, calibration and quality control. Patient scanning example may include: disabling (e.g. on the user interface and control software) calibration or QC techniques, if a patient was in the scanner, (e.g. as could be sensed by weight in the chair, etc.). Another example may include, if a patient is detected during calibration or QC, the calibration or QC processing that is underway would be interrupted, the x-ray disabled, and any rotation movement stopped. Another example may include, If a patient is detected, the software would prompt the user to enter the appropriate patient information (name, date of birth, etc) or select it from a prepopulated worklist. Another example may include, if a certain patient body part holder is connected, and/or body part detected, then the system would enable the corresponding scan protocol/technique. Another example may include, If patient movement is detected at the positioner, then the scanner can turn on a compensation image processing algorithm. Another example may include, if too much patient movement is detected (e.g. patient no longer present as detected from a weight sensor in the chair) then the scan could be interrupted, and the x-ray disabled and the rotation movement stopped. Yet another example may include, if the body part is a detected to be a brain (e.g. neuro head holder is plugged in) then the brain scan protocol could be enabled and bone/skull correction post processing algorithms could be made available or activated by default in the user interface. Yet another example may include, if the body part is a detected to be the teeth, (e.g. dental head holder is plugged in) then the metal artifact processing algorithms (for enamel or fillings) could be made available or activated by default in the user interface.

Other examples may be found in relation to calibration and quality control of the computed tomography system. One example may include that air calibration may require that no patient or other object be present. So, if the system detects a patient or object is present (or holder) then air calibration may be disabled. Another example may include that water calibration may require that a specific phantom (called a "water phantom") be placed in the scanner. This would warrant adjusting system parameters to include a large field of view, wide beam collimation, and a standard resolution (as opposed to high resolution) settings. Another example may include that geometry calibration may require a specific "geometry calibration phantom" is used. The system may adjust parameters to include a wide field of view, but in this case the system may be adjusted to have very high spatial resolution, and therefore, small detector pixels, large number of projection frames, etc. In yet another example the quality control function may require certain "QC phantom" test objects be placed in the field of view which have different attributes. Some are looking for low contrast features and others are looking for uniformity, image noise, etc. For example the ARC Head Phantom (American college of radiology or the CATPHAN (from Phantom Labs) are standard phantoms with many test modules. Each may require specific scan settings and could be detected from the holder. Each of these calibration and performance monitoring steps may only be available (or automatically initiated) if the corresponding phantom is placed in the scanner and/or sensed by a calibration identification through attachment to the accessory port like the patient positioning surface or through sensor confirmation like imaging or other sensed data.

Further, each of the sensed variable may be compared to one another to verify proper system setup and verify inferred conditions. If there is a mismatch or conflict in implied condition between sensors the user interface may issue a warning. For example, if the head/brain patient support body part holder is plugged in but a reasonable patient weight is not detected in the chair, then this condition could be reported, or scanning could be disabled.

Figure 4A:
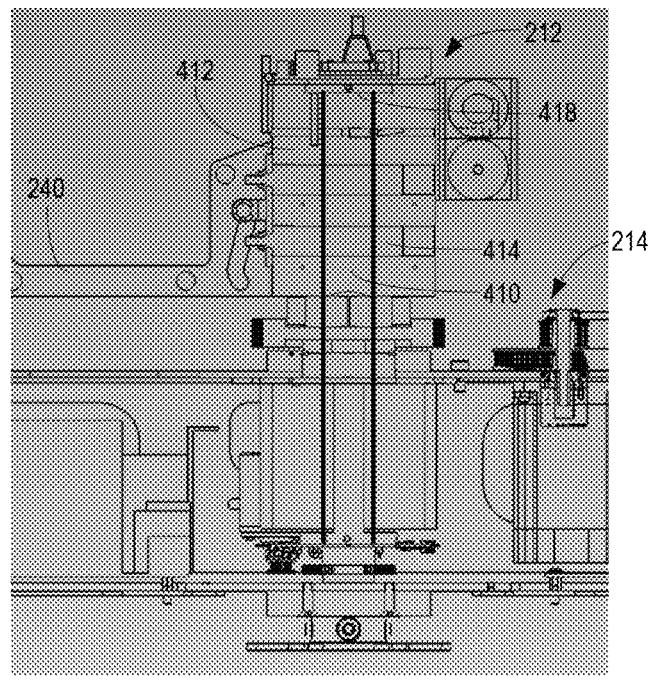
FIG. 4a is a sectional view of the socket assembly receiving the gantry assembly with the socket assembly unlocked.

FIG. 4A is a sectional view of the socket assembly 212 receiving the gantry assembly 214 with the socket assembly 212 being unlocked. In this figure, the handle 240 is up allowing a ball bearing attached to the pins to be at one end of a serpentine pathway where the pins are withdrawn. The gantry 214 includes a spindle 410 that may be inserted into a socket 412 allowing the socket assembly 212 to support and fix the position of the gantry assembly 214. Pins 414 may engage grooves 416 in the spindle 410 to lock the gantry assembly 214 within the socket assembly 212. Further, the socket assembly 212 may include conductive contacts 418 that form an electrical connection (e.g. physical contact) with conductive contacts in the spindle 410 of the gantry assembly to provide power to the gantry and communicate data between the gantry, the base, and remote stations. The communicated data may include control signals, sensor data, video data from the detector, or other signals that need to be transmitted between the base assembly and the gantry assembly. The conductive contacts 418 may be forced in to physical contact with the conductive contacts in the spindle by the locking mechanisms that mechanically lock the spindle in place within the socket.

Figure 4B:
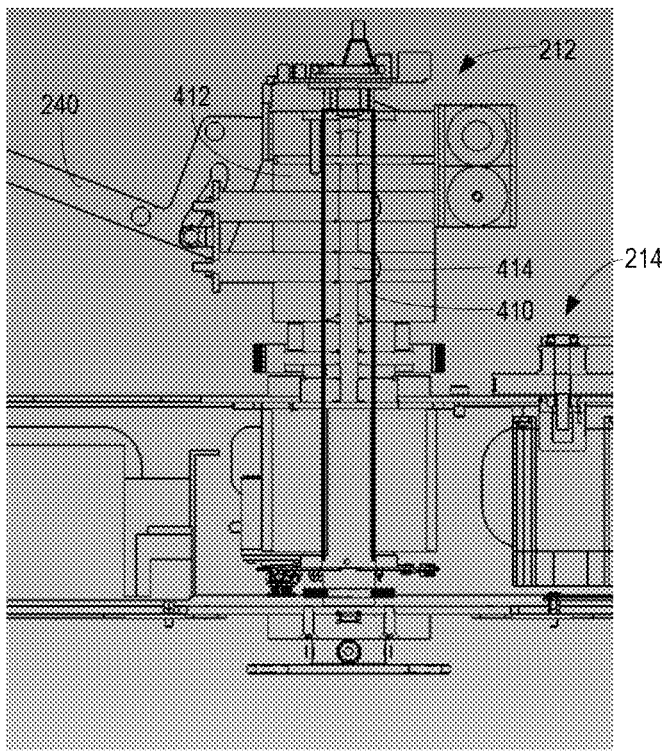
FIG. 4b is a sectional view of the socket assembly receiving the gantry assembly with the socket assembly locked.

FIG. 4B is a sectional side view illustrating socket assembly being in the locked position. Again, the spindle 410 of the gantry assembly 214 is inserted into the socket 412 of the socket assembly 212. When the handle 240 is pushed downward, the ball bearing attached to the pins 414 travels to the other side of the serpentine pathway pushing the pins 414 forward such that the pins 414 engage the grooves 416 in the spindle 410, thereby locking the spindle 410 within the socket 412.

Figure 5A:
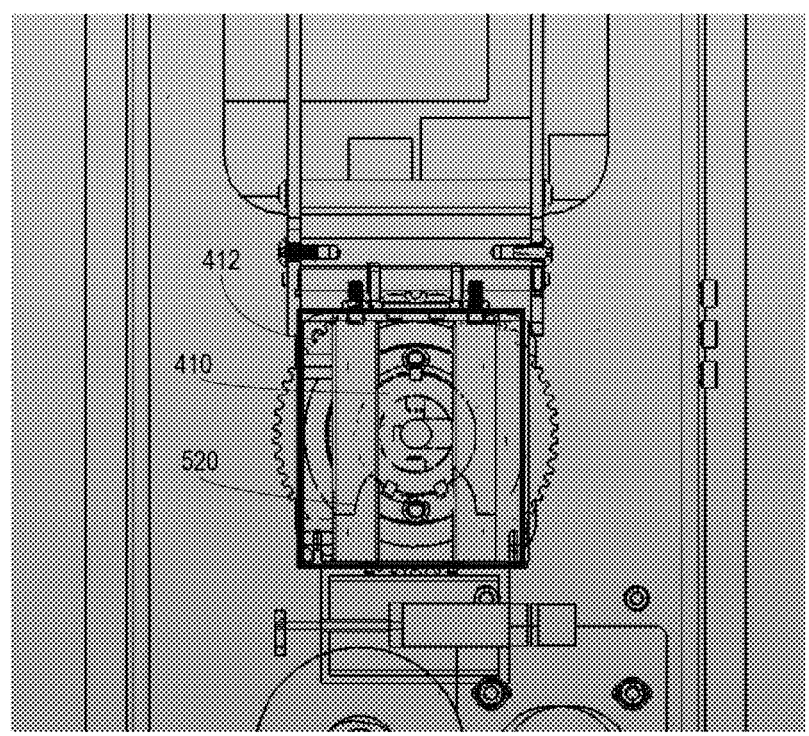
FIG. 5A is a sectional front view of the socket assembly in the unlocked position.

FIG. 5A is a sectional front view of the socket assembly in the unlocked position. The spindle 410 is shown from its end within the socket 412. The pins 414 are withdrawn from the grooves 416 in the spindle 410. Further, the pins include a circular cutout 510 that may match the radius of the spindle 410.

Figure 5B:
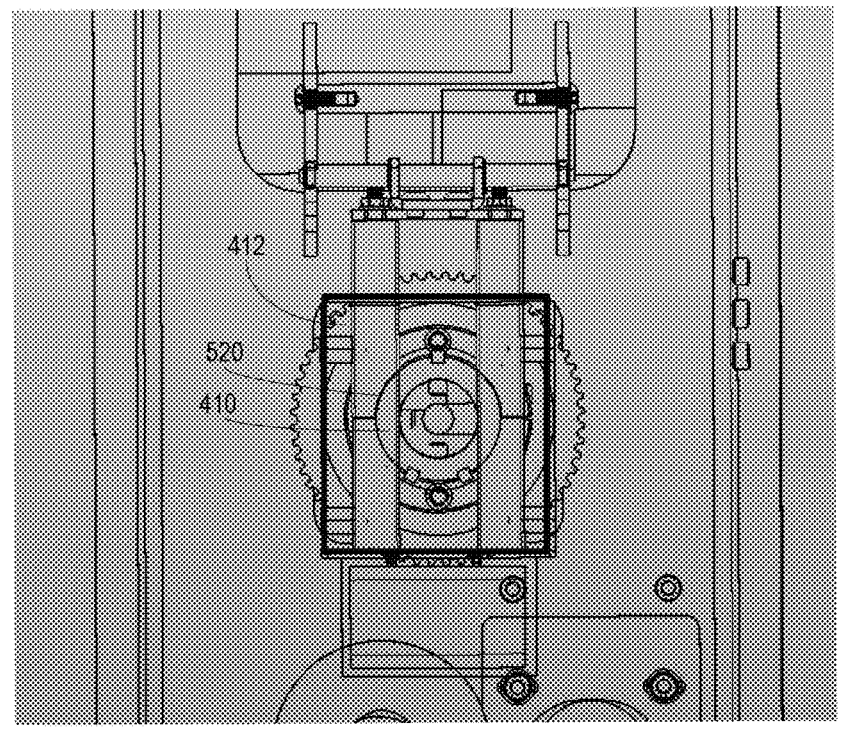
FIG. 5B is a sectional front view of the socket assembly in the locked position.

FIG. 5B illustrates a sectional front view of the socket assembly 212 in the locked position. In the locked position, the pins 414 are pushed forward to engage the grooves 416 in the spindle 410 in addition, the circular cutouts 510 in the pins 414 can be seen extending beyond the spindle 410.

Figure 6A:
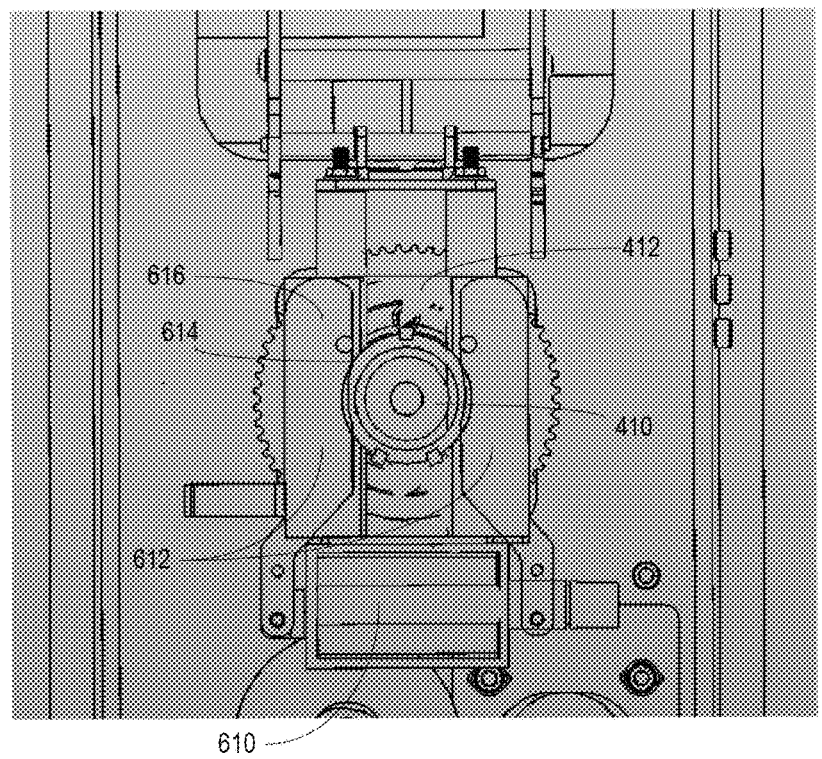
FIG. 6A is a front view illustrating safety levers in the unlocked position.

FIG. 6A is a front view illustrating safety levers 612 in an unlocked position. The safety levers 612 may engage grooves in the spindle 410 that move to the locked position. The levers 612 may be actuated by a solenoid 610. The solenoids 610 may push the levers outward when energized as denoted by arrows 620. The levers 612 may include a circular cutout that matches the diameter of the spindle 410 such that the spindle may be removed from the socket without interference from the levers 612 when the levers are in the unlocked position.

Figure 6B:
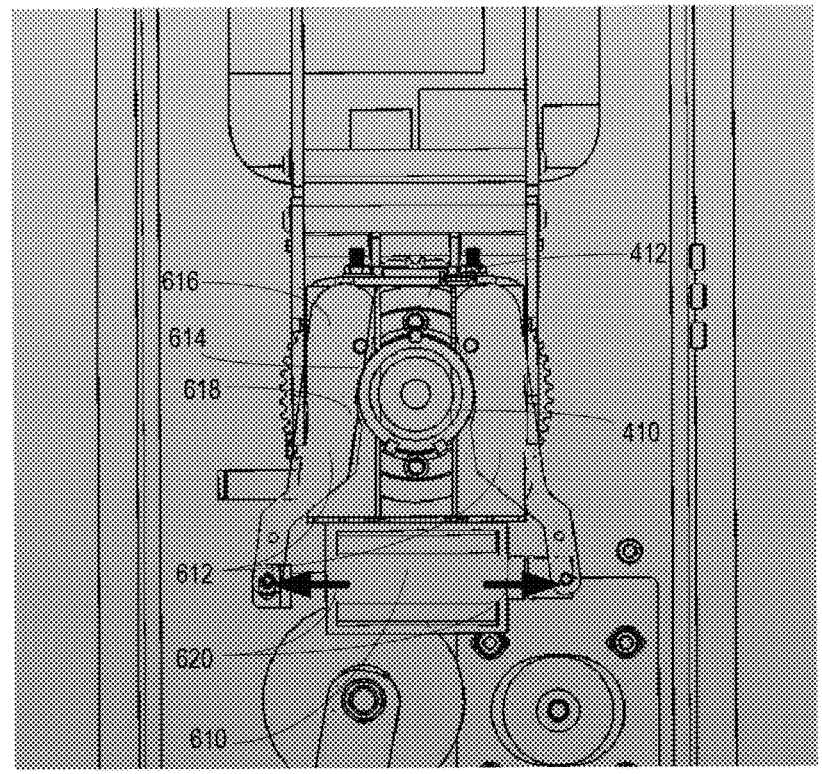
FIG. 6B is a front view illustrating safety levers in the locked position.

FIG. 6B illustrates the safety levers 612 in a locked position. In the locked position, the safety levers 612 engage grooves 614 in the spindle 410. The safety levers 612 may rotate about hinge plates 616 when the solenoids 610 are activated or deactivated. The solenoid 610 may be designed such that when the solenoid loses power and/or is in its most common failure mode, the safety levers 612 are biased into the locked position thereby engaging the spindle 410.

Figure 7A:
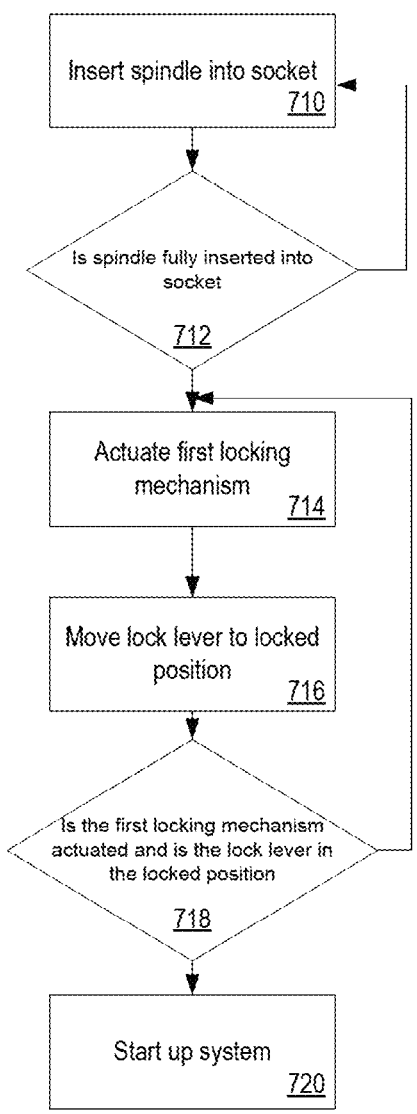
FIG. 7A is a flow chart of the method for attaching the gantry assembly to the base assembly.

FIG. 7A is a flowchart of a method for attaching the gantry assembly to the base assembly. The spindle of the gantry assembly may be inserted into the socket attached to the base assembly in block 710. A sensor may determine if the spindle is fully inserted into the socket as denoted by block 712. If the spindle is not fully inserted, the method would require the spindle to be fully inserted in block 710. If the spindle is fully inserted into the socket, the method would proceed to block 714. In block 714, the first locking mechanism may be actuated by a controller in the base assembly or socket assembly. The first locking mechanism may, for example, be levers that are actuated by a solenoid to engage the spindle. Although other locking mechanisms such as pins, etc. may be used. In block 716, the lock lever may be moved to the locked position. Moving the lock lever to the locked position may engage the spindle with a second locking mechanism, for example, pins that engage grooves in the spindle. In block 718, the system may determine if the first locking mechanism is actuated and if the lock lever is in the locked position. These conditions may be determined by sensors in the socket assembly. If the first locking mechanism is actuated and if the lock lever is in the locked position, the system may be started up and power may be provided to the gantry assembly from the socket assembly, as denoted by block 720.

Figure 7B:
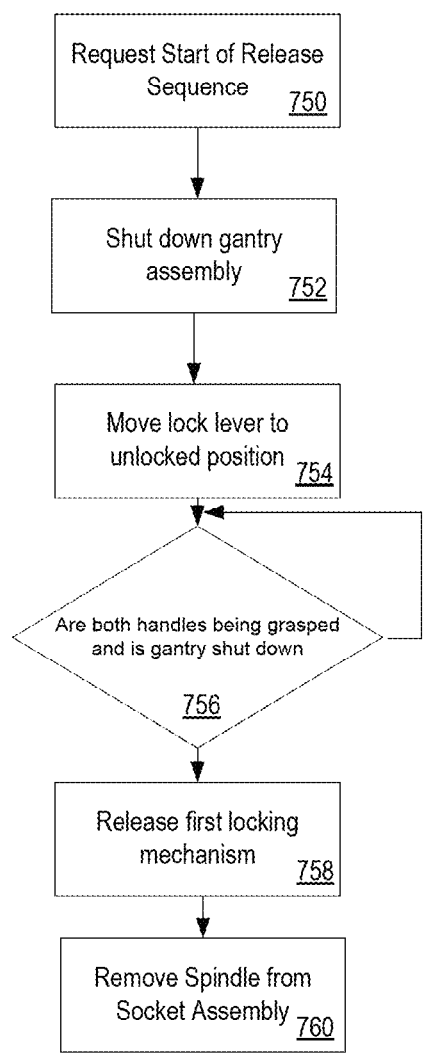
FIG. 7B is a flow chart of the method for detaching the gantry assembly from the base assembly.

FIG. 7B is a flowchart of a method for detaching the gantry assembly from the base assembly. The user may request a start of the release sequence, in block 750. The request may be made by selecting a choice on a user interface, pushing a button, or possibly in some implementations by moving the lock lever to the unlocked position. The system may shut down the gantry assembly in block 752. The shut down may include positioning or locking any motors, saving any data, shutting down any computers or processors, as well as, removing power from components in the gantry assembly. The lock lever may be moved to the unlocked position as denoted by block 754. One or more sensors may determine if the handles are being grasped and if the gantry is shut down, in block 756. The gantry assembly may be fairly heavy, therefore, it is helpful to check if the each of the handles is being grasped before it is released. This provides added protection that the gantry assembly is not damaged and that it does not fall on any of the persons removing it from the base assembly. If the handles are being grasped and if the gantry is shut down, the first locking mechanism may be released in block 758. With the first locking mechanism disengaged from the spindle, the spindle can be removed from the socket assembly in block 760.

Figure 8:
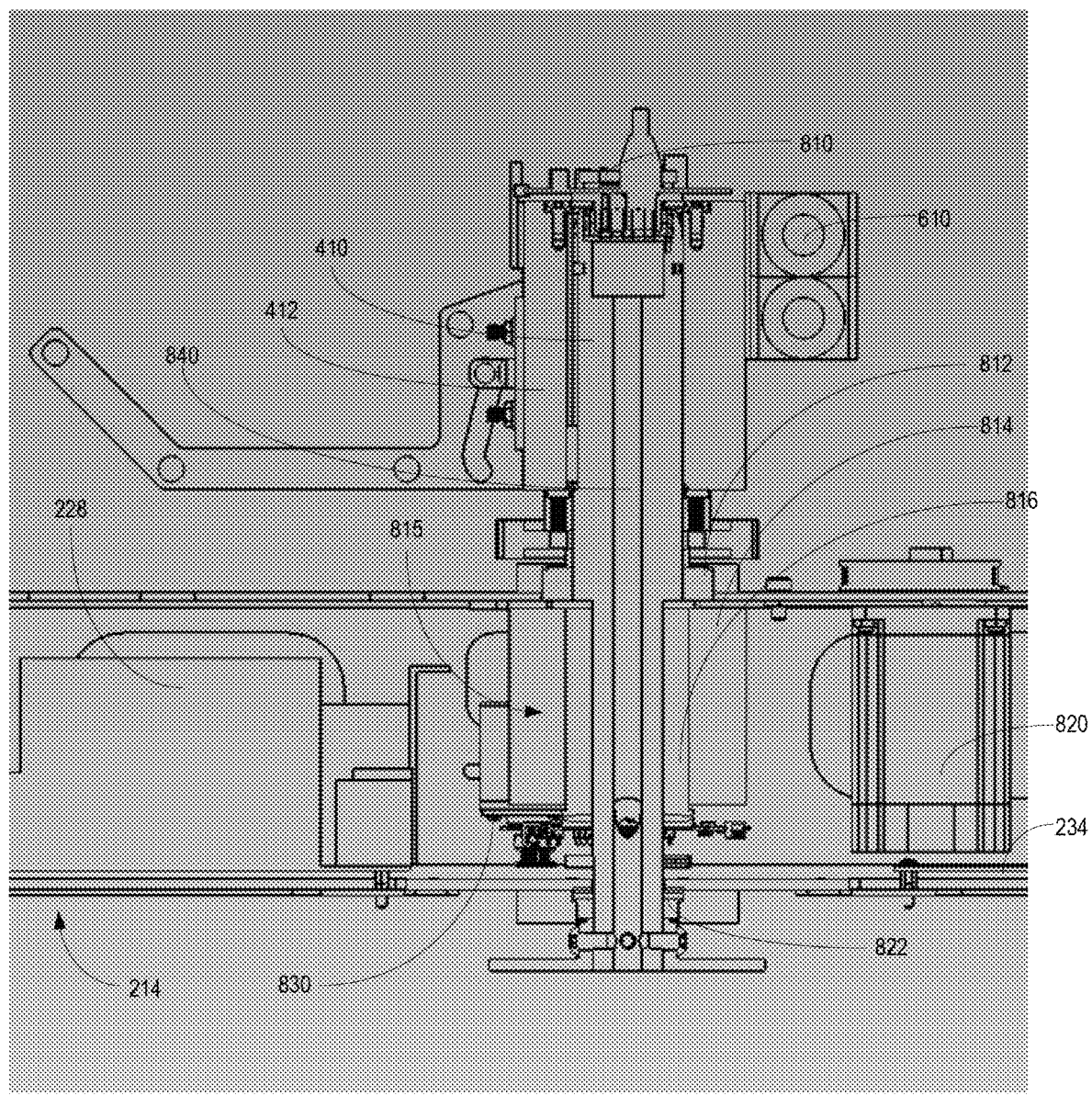
FIG. 8 illustrates the wiring flow between the socket assembly and the gantry assembly.

FIG. 8 illustrates the wiring flow between the socket assembly 212 and the gantry assembly 214. As discussed previously, the gantry assembly 212 includes a spindle 412 that is inserted into a socket 412 of the socket assembly 212. The socket assembly 212 includes a circuit assembly 810 for example, including a top PCB and USB connector. External wiring connections may be made to the circuit assembly 810. Electronics in the circuit assembly 810 may control actuation and deactuation of the interlock solenoid 610. The gantry assembly 214 may include a rotation motor 820 configured to rotate the gantry assembly 214 relative to the socket assembly 212. In some implementations, the gantry frame may rotate based on the rotation motor 820 about the spindle 410 while the spindle 410 remains stationary. As such, the spindle 410 may be seated against an upper bearing 812 attached to the gantry frame and a lower bearing 822 attached to the opposite side of the gantry frame. Accordingly, the wiring from the circuit assembly 810 may be fixed and remain stationary as it is fed through a bore 840 in the spindle and out holes near the lower bearing 822. The wiring may then connect to a stationary portion 816 of the slip ring 815 that communicates the electrical signals to a rotating portion 814 to the slip ring 815. Accordingly, the electrical signals may be communicated from the stationary socket assembly 212 to portions of the gantry assembly 214 that rotate about the spindle 410, for example including onboard computer 228. The bottom circuit assembly 830 is connected to the wiring as it exits the bore 840 in the spindle 410. The circuit assembly 830 is connected to a stationary portion 816 of the slip ring 815. Signals and power are transferred from the stationary portion 816 of the slip ring 815 to the rotating portion 814 of the slip ring 815. The rotating portion 816 of the slip ring 815 connects to the onboard PC and the distribution board both of which may rotate with the gantry assembly 214 while the spindle 410 remains stationary.

Figure 9:
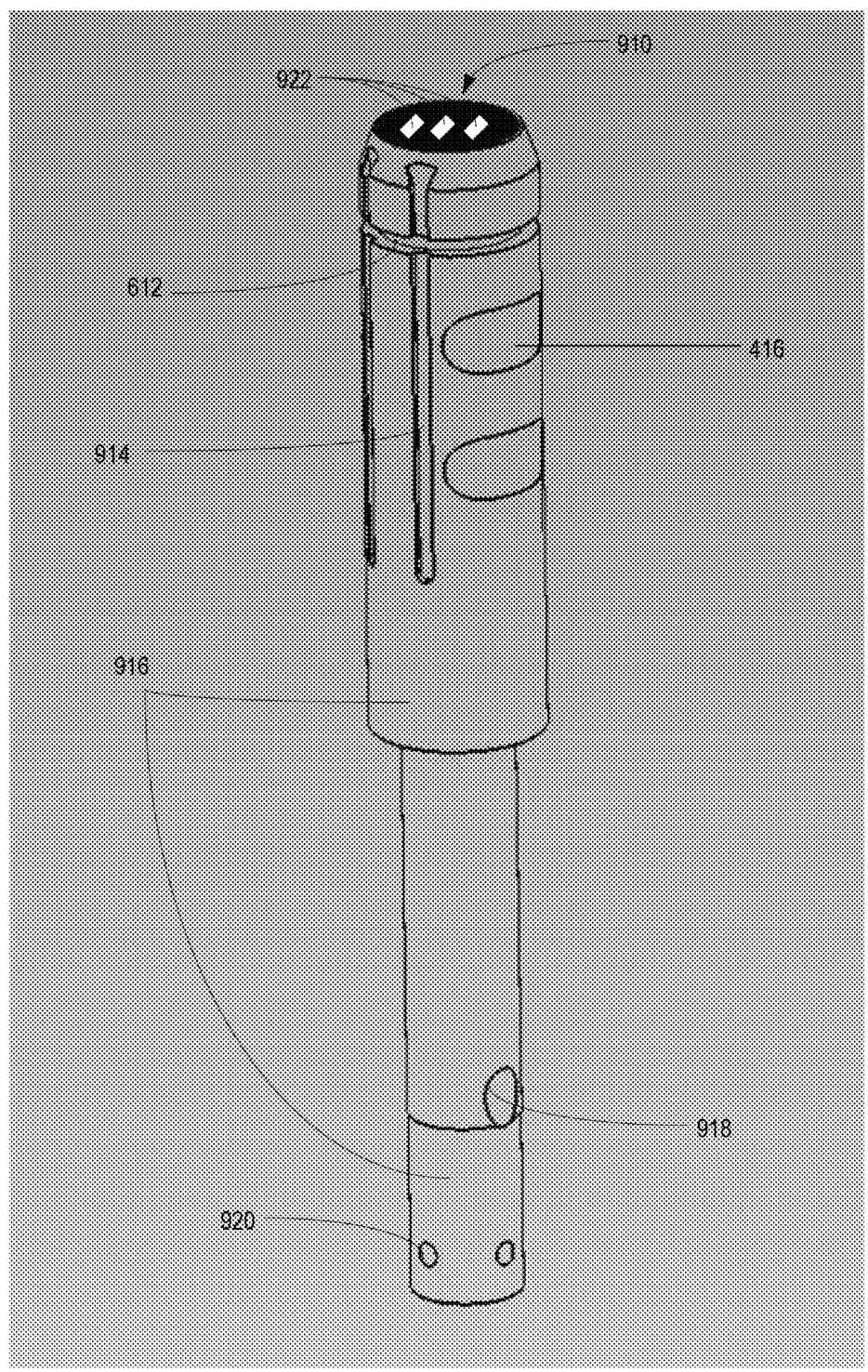
FIG. 9 is a perspective view of the spindle.

FIG. 9 is a perspective view of the spindle 410. The spindle may include an opening 910 in the end of the spindle where wiring may enter and threads may secure to a connector or the circuit assembly 810. The spindle 410 may include cutouts 416 for the main lock pins 414. In addition, the spindle 410 may include alignment grooves 914 that run along the length of the spindle. In addition, the spindle may include grooves 912 that are configured to engage the interlock lever 612.

The alignment grooves 914 control the orientation of the gantry assembly 214 as the spindle 410 is inserted into socket 412. In additional, the spindle may include bearing surfaces 916 which may be made of the same or a different material than the rest of the spindle 410. For example, the bearing surfaces 916 may be coated differently than other surfaces of the spindle. In addition, the spindle includes fastening holes 920 where a bearing retainer may be attached to the spindle 410. The spindle 410 may include an opening 918 near the load bearing surface where the wires exit the bore of the spindle and may attach to the lower circuit assembly 830. Further, the spindle (e.g. the end of the spindle) may include conductive contacts 922 that form an electrical connection (e.g. physical contact) with conductive contacts in the socket to provide power to the gantry and communicate data between the gantry assembly, the base assembly, and remote stations. The conductive contacts 922 may be forced in to physical contact with the conductive contacts in the socket by the locking mechanisms that mechanically lock the spindle in place within the socket.

Figure 10:
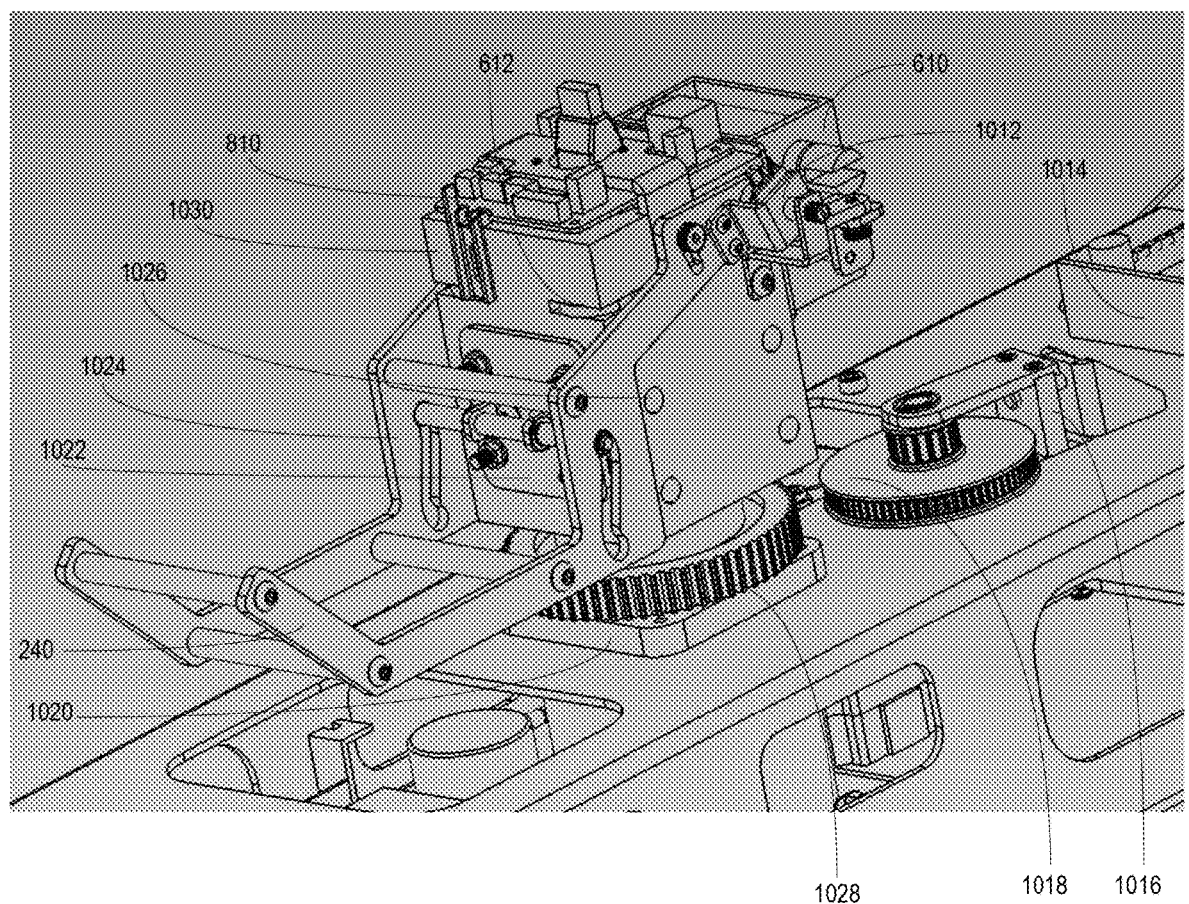
FIG. 10 is a perspective view of the socket assembly.

FIG. 10 is a perspective view of the socket assembly 212. As previously discussed, the socket assembly includes safety interlock levers 612 that may be actuated by interlock solenoids 610. The solenoids may be driven by the circuit assembly 810. The socket assembly 212 may include a sensor 1012 for example, a potentiometer that monitors a position of the lock handle 240. The safety interlocks will not release if the lock handle 240 is in the locked position as determined by a threshold measure of the potentiometer reading. The rotation motor driver 1014 may control the motor in the gantry assembly 214. The motor may connect to a rotation driver assembly 1018 through a pulley system that uses a belt tensioner assembly 1016. The rotation driver assembly 1018 interacts with the main drive pulley 1028 to provide rotation of the gantry assembly 214 relative to the socket assembly 212. The upper bearing retainer 1020 positions the upper bearing relative to the spindle 410. The handle 240 may interact with a plate 1022 that inserts or retracts the lock pins 414. The handle 240 may include a lock lever 1024 to lock the position of the handle 240. The socket assembly 212 may include threaded holes 1026 for mounting bolts allowing the socket assembly 212 to be attached to various stands as discussed with regard to FIG. 1. In addition, the socket assembly 212 may include optical switches to monitor the state of the circuit assembly 812. For example, to determine if the circuit assembly 812 is connected or disconnected from a wiring assembly.

Figure 11:
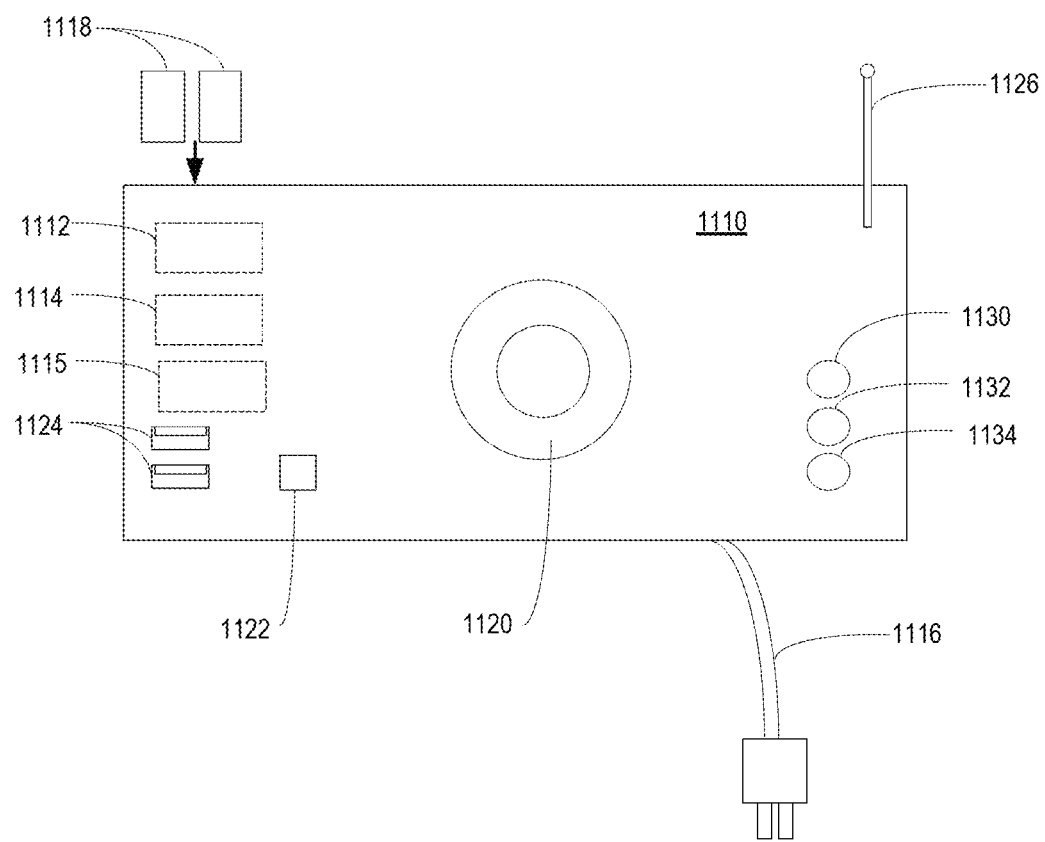
FIG. 11 is a block diagram of a base control unit.

FIG. 11 is a block diagram of one implementation of a base control unit. The base assembly may include a base control unit 1110. The base control unit may include power conditioning electronics 1112 (e.g. an uninterruptible power supply) and control circuitry 1114. The control circuitry may include one or more processors as discussed throughout and may be in communication with a data storage unit 1115. The control circuitry 1114 may be connected to a display device and input device providing a user interface to adjust system parameters or view data. The base control unit 1110 may include an AC power plug 1116 to provide power to the base assembly as well as the gantry assembly. The base control unit 1110 may include one or more batteries 1118, for example rechargeable batteries that may be automatically recharged within the base control unit 1110 when the AC power plug 1116 is connected to power or separately by a charging station if removed from the base control unit 1110. The batteries 1118 may be easily accessible and user changeable via a panel in the base control unit 1110. The base control unit 1110 may include controls 1120 to manipulate the functions of the base assembly or the gantry assembly (e.g. adjust socket height, adjust the gantry position, control various functions of the x-ray source or detector, request disengagement of the gantry assembly, etc.). The base control unit 1110 may facilitate communications with or from the base assembly and/or the gantry assembly by providing USB (universal serial bus) connections 1124, Ethernet connections 1126, wireless connections 1128 (e.g. WiFi, Bluetooth, cellular, or similar wireless communications) or other similar communication connections. Further, the base control unit may have a display including indicators or even a display and keyboard. For example, the base control unit 1110 may include a power indicator 1130, a network indicator 1132, and a status indicator 1134.

Figure 12:
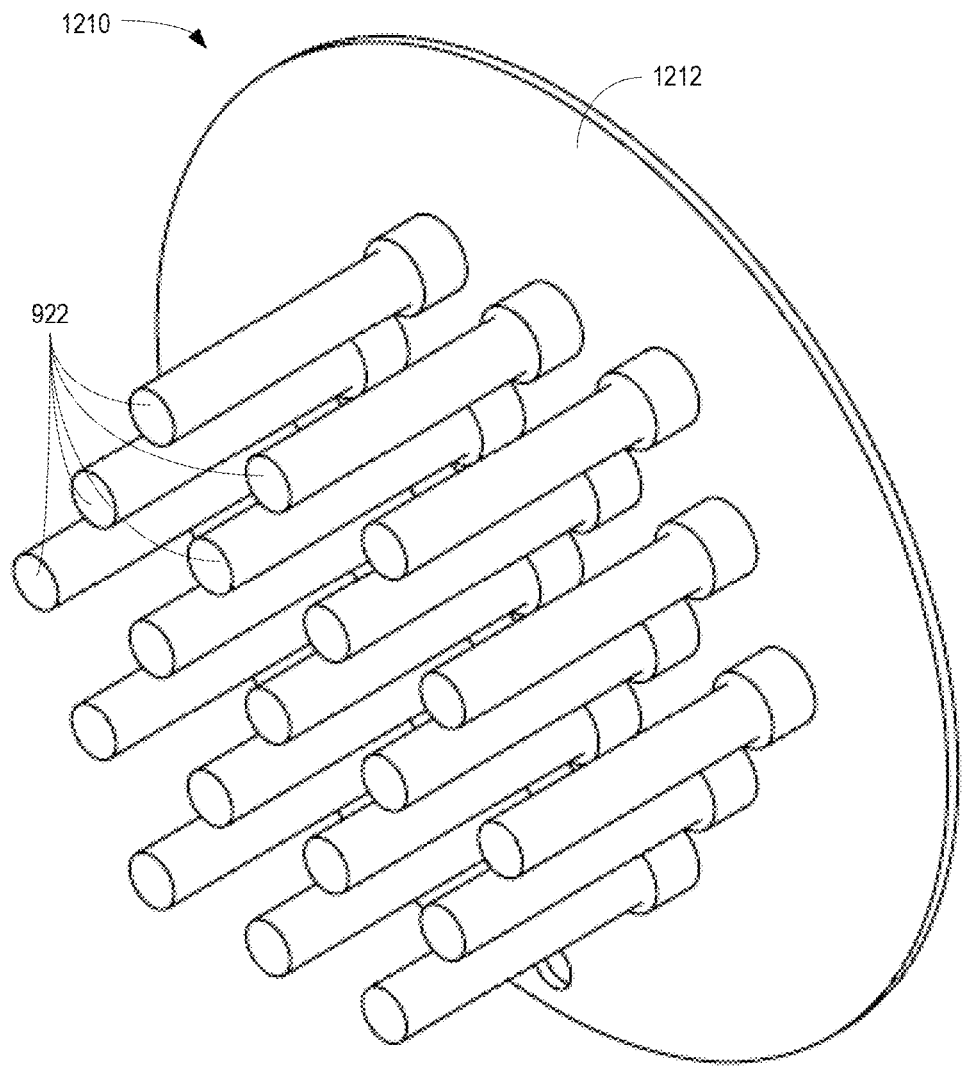
FIG. 12 is a perspective view of a conductor assembly.

FIG. 12 is a perspective view of a conductor assembly 1210. The conductor assembly 1210 may include conductive contacts 922 and a board 1212. The board 1212 may provide structural support for the conductive contacts 922 and in some implementations may also include conductive traces or electrical components connected to the conductive contacts 922. The conductive contacts 922 may be pins made of an electrically conductive material and may be spring loaded.

Further, the conductor assembly 1210 may be integrated into the spindle (e.g. the end of the spindle) such that conductive contacts 922 form an electrical connection (e.g. physical contact) with conductive contacts in the socket to provide power to the gantry and communicate data between the gantry, the base, and remote stations. The conductive contacts 922 may be forced in to physical contact with the conductive contacts in the socket by the locking mechanisms that mechanically lock the spindle in place within the socket.

The methods, devices, processors, modules, engines, and logic described above may be implemented in many different ways and in many different combinations of hardware and software. For example, all or parts of the implementations may be circuitry that includes an instruction processor, such as a Central Processing Unit (CPU), microcontroller, or a microprocessor; an Application Specific Integrated Circuit (ASIC), Programmable Logic Device (PLD), or Field Programmable Gate Array (FPGA); or circuitry that includes discrete logic or other circuit components, including analog circuit components, digital circuit components or both; or any combination thereof. The circuitry may include discrete interconnected hardware components and/or may be combined on a single integrated circuit die, distributed among multiple integrated circuit dies, or implemented in a Multiple Chip Module (MCM) of multiple integrated circuit dies in a common package, as examples.

The circuitry may further include or access instructions for execution by the circuitry. The instructions may be stored in a tangible storage medium that is other than a transitory signal, such as a flash memory, a Random Access Memory (RAM), a Read Only Memory (ROM), an Erasable Programmable Read Only Memory (EPROM); or on a magnetic or optical disc, such as a Compact Disc Read Only Memory (CDROM), Hard Disk Drive (HDD), or other magnetic or optical disk; or in or on another machine-readable medium. A product, such as a computer program product, may include a storage medium and instructions stored in or on the medium, and the instructions when executed by the circuitry in a device may cause the device to implement any of the processing described above or illustrated in the drawings.

The implementations may be distributed as circuitry among multiple system components, such as among multiple processors and memories, optionally including multiple distributed processing systems. Parameters, databases, and other data structures may be separately stored and managed, may be incorporated into a single memory or database, may be logically and physically organized in many different ways, and may be implemented in many different ways, including as data structures such as linked lists, hash tables, arrays, records, objects, or implicit storage mechanisms. Programs may be parts (e.g., subroutines) of a single program, separate programs, distributed across several memories and processors, or implemented in many different ways, such as in a library, such as a shared library (e.g., a Dynamic Link Library (DLL)). The DLL, for example, may store instructions that perform any of the processing described above or illustrated in the drawings, when executed by the circuitry.

As a person skilled in the art will readily appreciate, the above description is meant as an illustration of implementation of the principles this disclosure. This description is not intended to limit the scope or application of this system in that the system is susceptible to modification, variation and change, without departing from the spirit of this disclosure, as defined in the following claims.

I/We claim:

1. A computed tomography system comprising:
a gantry assembly having a x-ray source, and a x-ray imager;
a base assembly configured to receive power and provide mechanical stability;
a connection interface between the gantry assembly and the base assembly, the connection interface having a first locking mechanism configured to mechanically lock the gantry assembly to the base assembly, the connection interface configured to provide power to the gantry assembly through the base assembly, wherein the gantry assembly is detachable from the base assembly when the first locking mechanism is unlocked.

2. The system according to claim 1, further comprising a socket assembly and a spindle, the socket assembly having the first locking mechanism and configured to receive the spindle to mechanically lock the gantry assembly to the base assembly.

3. The system according to claim 2, further comprising a spindle sensor configured to determine when the spindle is fully inserted into the socket assembly, a controller being configured to actuate the first locking mechanism which engages the spindle to mechanically lock the gantry assembly to the base assembly in response to the spindle sensor.

4. The system according to claim 3, wherein the first locking mechanism is a lever attached to the socket assembly and actuated by a solenoid to engage the spindle.

5. The system according to claim 2, wherein the spindle is stationary and the gantry assembly includes a motor configured to rotate the gantry assembly around the spindle.

6. The system according to claim 5, further comprising a patient positioning surface attached to the spindle for maintaining a position of a region to be imaged with the gantry assembly.

7. The system according to claim 1, further comprising a lock lever, the lock lever being attached to a second locking mechanism that locks the gantry assembly to the base assembly when the lock lever is in a locked position, the second locking mechanism releasing the gantry assembly from the base assembly when the lock lever is in an open position.

8. The system according to claim 7, further comprising a socket assembly and a spindle, the socket assembly having the first locking mechanism and configured to receive the spindle to mechanically lock the gantry assembly to the base assembly, wherein the second locking mechanism comprises pins that engage the spindle.

9. The system according to claim 7, further comprising a lock lever sensor that determines whether the lock lever is in the locked position.

10. The system according to claim 1, further comprising at least two handles, each handle including at least one handle sensor to determine when the handle is being grasped.

11. The system according to claim 10, wherein the at least one handle sensor is a touch sensor.

12. The system according to claim 10, wherein a controller is configured to unlock the first locking mechanism to detach the gantry assembly from the base assembly in response to each of the at least one handle sensor being grasped.

13. The system according to claim 1, further comprising a user interface connected to the base assembly and configured to receive image data from the gantry assembly through the base assembly.

14. The system according to claim 1, further comprising a user interface connected to the base assembly and configured to receive a signal identifying a type of gantry assembly indicating features of the gantry assembly, the user interface enabling or disabling controls of the user interface in response to the type of gantry assembly.

15. The system according to claim 1, wherein the base assembly is configured to receive a signal identifying a type of gantry assembly indicating features of the gantry assembly, the base assembly adjusting control parameters in response to the type of gantry assembly.

16. The system according to claim 1, further wherein the gantry assembly receives data about a position or orientation of the connection interface from the base assembly.

17. The system according to claim 1, further comprising a socket assembly and a spindle, the socket assembly having the first locking mechanism and being configured to receive the spindle to mechanically lock the gantry assembly to the base assembly, wiring electronically connecting the base assembly to the gantry assembly through the spindle such that the spindle remains stationary and a slip ring is electrically connected between the wiring in the spindle and the gantry assembly.

18. A method for mounting a detachable imaging module of a computed tomography system, the method comprising the steps of:

inserting a spindle of a gantry assembly into a socket assembly attached to a base assembly;
sensing insertion of the spindle into the socket assembly;
actuating a first locking mechanism to secure the position of the gantry assembly to the base assembly in response to the sensing insertion of the spindle;
providing power to the gantry assembly in response to the actuating of the first locking mechanism.

19. The method according to claim 18, further comprising the steps of:
moving a locking lever into a locked position such that a second locking mechanism engages the spindle;
sensing the locking lever is in the locked position;
providing power to the gantry assembly in response to sensing the locking lever is in the locked position.

20. The method according to claim 18, further comprising the steps of:
sensing that a plurality of handles are being grasped;
deactivating the first locking mechanism to disengage the gantry assembly from the base assembly in response to the sensing that the plurality of handles are being grasped.

21. A computed tomography system comprising:
a gantry assembly having a motor, a x-ray source, and a x-ray imager;
a base assembly configured to receive power and provide mechanical stability;
a socket assembly attached to the base assembly, the gantry assembly comprising a spindle, the socket assembly being configured to receive the spindle to mechanically lock the gantry assembly to the base assembly, wiring electronically connecting the base assembly to the gantry assembly through the spindle such that the spindle remains stationary and the motor being configured to rotate the gantry assembly around the spindle.

22. A computed tomography system comprising:
a gantry assembly having a x-ray source, and a x-ray imager;
a base assembly configured to receive power and provide mechanical stability;
a connection interface between the gantry assembly and the base assembly, the connection interface having a first locking mechanism configured to mechanically lock the gantry assembly to the base assembly, the connection interface configured to supply electrical connections that provide power to the gantry assembly through the base assembly and transmit data between the gantry assembly and base assembly, wherein the gantry assembly is detachable from the base assembly when the first locking mechanism is unlocked.

23. The computed tomography system according to claim 22, wherein the gantry assembly includes at least one sensor that is configured to sense and transmit at least one of a type of gantry, type of calibration object, type of patient positioning surface, type of body part being measured, motion, acceleration, position, lock status, image data, and patient size or weight to the base assembly.

24. The computed tomography system according to claim 22, wherein the base assembly includes at least one sensor configured to sense and transmit at least one of motion, acceleration, vibration, tilt, ambient temperature, base temperature, power supply status, voltage, current, power, position, and lock status to the gantry assembly.

* * * * *